(12) United States Patent
Hao et al.

(10) Patent No.: US 11,553,858 B2
(45) Date of Patent: Jan. 17, 2023

(54) MOBILITY ANALYSIS

(71) Applicant: INTERNATIONAL BUSINESS MACHINES CORPORATION, Armonk, NY (US)

(72) Inventors: Tian Hao, White Plains, NY (US); Jeffrey L. Rogers, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 251 days.

(21) Appl. No.: 16/941,907

(22) Filed: Jul. 29, 2020

(65) Prior Publication Data
US 2022/0031199 A1 Feb. 3, 2022

(51) Int. Cl.
*A61B 5/00* (2006.01)
*A61B 5/11* (2006.01)
*G16H 40/67* (2018.01)
*G16H 20/30* (2018.01)

(52) U.S. Cl.
CPC .......... *A61B 5/1122* (2013.01); *A61B 5/0004* (2013.01); *A61B 5/0024* (2013.01); *A61B 5/1117* (2013.01); *G16H 20/30* (2018.01); *G16H 40/67* (2018.01)

(58) Field of Classification Search
CPC ... A61B 5/1122; A61B 5/0004; A61B 5/0024; A61B 5/1117; A61B 5/4082; A61B 5/1113; G16H 20/30; G16H 40/67
See application file for complete search history.

(56) References Cited

U.S. PATENT DOCUMENTS

2017/0173262 A1 6/2017 Veltz
2019/0285740 A1* 9/2019 Boufounos .......... G01S 13/887
2021/0393166 A1* 12/2021 DeMers ................. A61B 5/112

FOREIGN PATENT DOCUMENTS

WO 2013003510 A1 1/2013

OTHER PUBLICATIONS

Gaitrite, "World Leader in Temporospatial Gait Analysis", https://www.gaitrite.com/, printed Dec. 27, 2019, pp. 1-3.
https://www.apdm.com/, "The Next Generation Opal" a research-grade wearable sensor, built for quantifying movement, APDM Wearable Techologies, printed Jul. 28, 2020, pp. 1-4.
Long et al., "Fusion of Millimeter Wave Radar and RGB-Depth Sensors for Assisted Navigation of the Visually Impaired", https://www.spiedigitallibrary.org/conference-proceedings-of-spie/10800 . . . , Millimetre Wave and Terahertz Sensors and Tech.,Oct. 5, 2018, pp. 1-14.
(Continued)

*Primary Examiner* — David J. McCrosky
*Assistant Examiner* — Nidhi N Patel
(74) *Attorney, Agent, or Firm* — Kristofer L. Haggerty

(57) ABSTRACT

A method, a structure, and a computer system for assessing user mobility. The exemplary embodiments may include collecting mobility data corresponding to a user and extracting one or more low level features from the mobility data. The exemplary embodiments may further include extracting one or more clinical level features from the low level features and assessing one or more health conditions of the user based on applying one or more models to the one or more clinical level features.

17 Claims, 5 Drawing Sheets

(56) References Cited

OTHER PUBLICATIONS

Mell et al., "The NIST Definition of Cloud Computing", National Institute of Standards and Technology, Special Publication 800-145, Sep. 2011, pp. 1-7.
Mikhelson et al., "Noncontact Millimeter-Wave Real-Time Detection and Tracking of Heart Rate on an Ambulatory Subject", IEEE Transactions on Information Technology in Biomedicine, vol. 16, No. 5, Sep. 2012, pp. 1-8.
Vicon, "Award Winning Motion Capture Systems", https://www.vicon.com/, printed Jul. 29, 2020, pp. 1-6.

* cited by examiner

MOBILITY ANALYSIS

BACKGROUND

The exemplary embodiments relate generally to user mobility, and more particularly to analysing user health through user mobility.

Mobility refers to one's ability to move freely and easily. Physiologically, mobility is a manifestation of a functional integration of skeletal, muscular, nervous, circulatory, and respiratory systems. Thus, mobility may represent critical clinical evidence in assessing physical and cognitive health, for example progression of neuro-degenerative diseases, quality of life, risk of fall, ability of independent living, and frailty of pre- and post-surgery patients.

SUMMARY

The exemplary embodiments disclose a method, a structure, and a computer system for assessing user mobility. The exemplary embodiments may include collecting mobility data corresponding to a user and extracting one or more low level features from the mobility data. The exemplary embodiments may further include extracting one or more clinical level features from the low level features and assessing one or more health conditions of the user based on applying one or more models to the one or more clinical level features.

BRIEF DESCRIPTION OF THE SEVERAL VIEWS OF THE DRAWINGS

The following detailed description, given by way of example and not intended to limit the exemplary embodiments solely thereto, will best be appreciated in conjunction with the accompanying drawings, in which.

The drawings are not necessarily to scale. The drawings are merely schematic representations, not intended to portray specific parameters of the exemplary embodiments. The drawings are intended to depict only typical exemplary embodiments. In the drawings, like numbering represents like elements.

DETAILED DESCRIPTION OF THE SEVERAL VIEWS OF THE DRAWINGS

Figure 1:
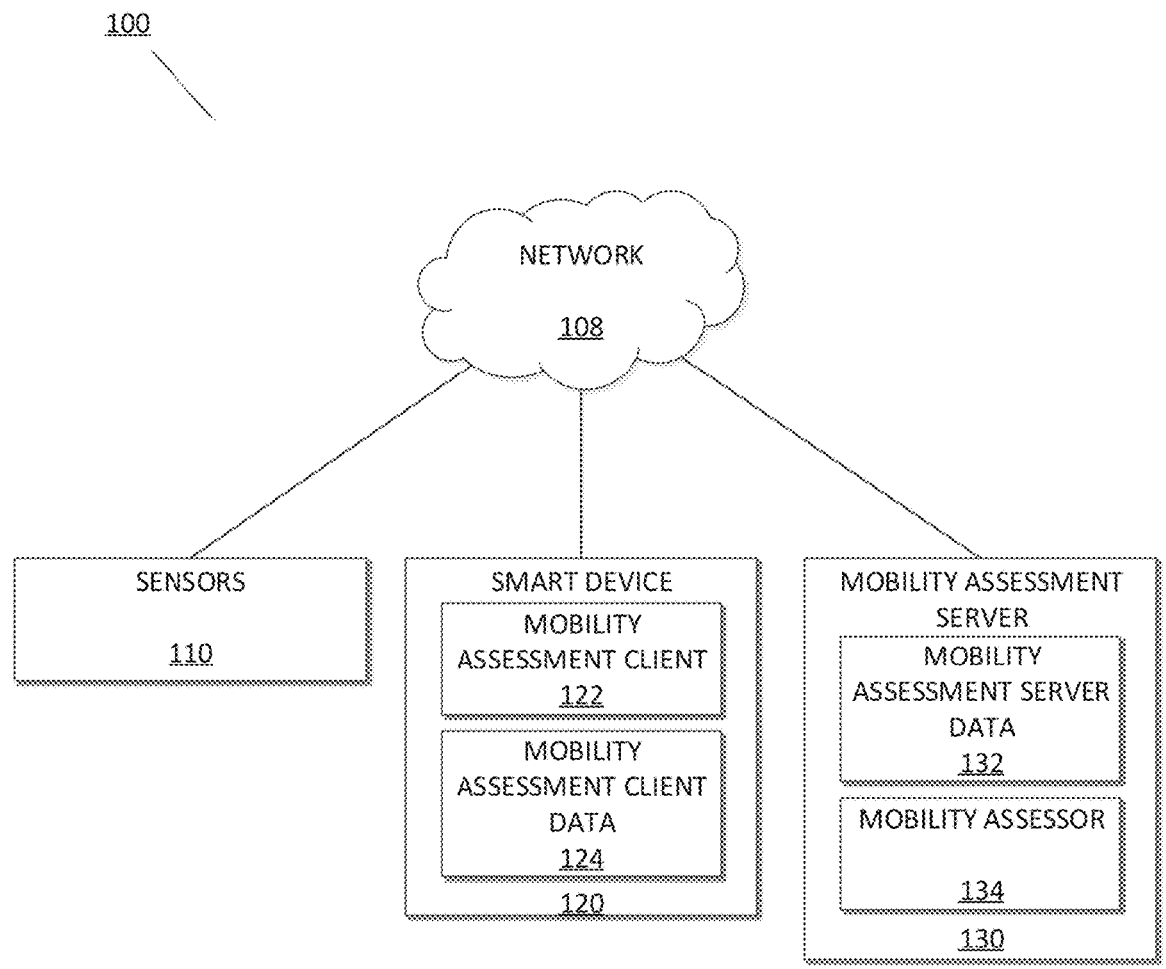
FIG. 1 depicts an exemplary schematic diagram of a mobility assessment system 100, in accordance with the exemplary embodiments.

Detailed embodiments of the claimed structures and methods are disclosed herein; however, it can be understood that the disclosed embodiments are merely illustrative of the claimed structures and methods that may be embodied in various forms. The exemplary embodiments are only illustrative and may, however, be embodied in many different forms and should not be construed as limited to the exemplary embodiments set forth herein. Rather, these exemplary embodiments are provided so that this disclosure will be thorough and complete, and will fully convey the scope to be covered by the exemplary embodiments to those skilled in the art. In the description, details of well-known features and techniques may be omitted to avoid unnecessarily obscuring the presented embodiments.

References in the specification to "one embodiment", "an embodiment", "an exemplary embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of the exemplary embodiments, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements according to the various exemplary embodiments.

Mobility refers to one's ability to move freely and easily. Physiologically, mobility is a manifestation of a functional integration of skeletal, muscular, nervous, circulatory, and respiratory systems. Thus, mobility may represent critical clinical evidence in assessing physical and cognitive health, for example progression of neuro-degenerative diseases, quality of life, risk of fall, ability of independent living, and frailty of pre- and post-surgery patients.

There are currently several means for analyzing user mobility that vary in complexity, scalability, and practicality. At a basic level, user mobility may be analyzed through self-reporting, for example daily or weekly questionnaires. Though inexpensive and easy to implement, self-reporting through questionnaires is lacking in both the data collected and an accuracy thereof. Alternatively, user mobility may be assessed through clinical mobility tests such as the timed up and go (TUG), 30-second chair stand, and 6-minute walk test (6MWT). However, in addition to presenting a burden on both patients and clinicians, these methods are also ineffective and fail to capture all relevant data.

Other means include light-weight solutions, such as on-body inertial sensors that directly measure and aggregate motion of various body parts of interest. While on-body inertial sensors may accurately report motion and posture, they require complex and burdensome setups, are not suitable for monitoring longitudinal motion, lack accuracy in location and trajectory tracking, and present relatively high costs for a scalable deployment. Current mobility assessment methods may also implement infrared cameras that measure depth based on the time-of-flight (ToF) of a projected infrared laser. While the benefits of these systems include contactless sensing and the ability to reveal body details such as a body frame, their shortcomings include a required line of sight, and thus limited coverage/a narrow field of view, as well as subjectivity to lighting and environmental conditions.

Other mobility assessment solutions may be performed in a clinical setting where pressure mapping systems may be used to capture foot pressure of a walking user to provide a variety of gait parameters. These systems, however, are impractical for consistent use due to their complex setup and operation, as well as high cost. Similarly, more complex systems may track retro-reflective markers placed on a moving body using infrared cameras located around the clinical setting. These systems too, however, are impractical for consistent use and are not easily scaled due to their complex setup and high costs.

There is thus a need for a contactless, inexpensive, scalable, and less burdensome solution to assess various user mobility parameters consistently and accurately. Accordingly, the forthcoming detailed description presents a system for motion tracking user mobility using a combination of millimeter wave sensors and depth cameras, as well as an architecture that aggregates and analyses the motion tracking data for continuously captured low-level motion features. Benefits of the proposed motion tracking system include practicality and scalability in capturing user motion within a nonclinical setting in a manner that is contactless, passive, continuous, accurate, multidimensional, cost effective, and easy to use. Moreover, benefits of the aggregation and analysis architecture include support for a wide range of assessments, such as progression of neuro-degenerative disease, quality of life, fall risk, frailty, etc., as well as the ability to create predictive models through machine learning of the collected large-scale and multidimensional motion tracking data. Detailed description of the invention follows.

FIG. 1 depicts the mobility assessment system 100, in accordance with exemplary embodiments. According to the exemplary embodiments, the mobility assessment system 100 may include one or more sensors 110, a smart device 120, and a mobility assessment server 130, which all may be interconnected via a network 108. While programming and data of the exemplary embodiments may be stored and accessed remotely across several servers via the network 108, programming and data of the exemplary embodiments may alternatively or additionally be stored locally on as few as one physical computing device or amongst other computing devices than those depicted. The operations of the mobility assessment system 100 are described in greater detail herein.

In the exemplary embodiments, the network 108 may be a communication channel capable of transferring data between connected devices. In the exemplary embodiments, the network 108 may be the Internet, representing a worldwide collection of networks and gateways to support communications between devices connected to the Internet. Moreover, the network 108 may utilize various types of connections such as wired, wireless, fiber optic, etc. which may be implemented as an intranet network, a local area network (LAN), a wide area network (WAN), or a combination thereof. In further embodiments, the network 108 may be a short-range wireless technology network, a Wi-Fi network, or a combination thereof. The network 108 may operate in frequencies including 2.4 gHz and 5 gHz internet, near-field communication, Z-Wave, Zigbee, etc. In yet further embodiments, the network 108 may be a telecommunications network used to facilitate telephone calls between two or more parties comprising a landline network, a wireless network, a closed network, a satellite network, or a combination thereof. In general, the network 108 may represent any combination of connections and protocols that will support communications between connected devices.

In exemplary embodiments, the sensors 110 may be one or more devices capable of collecting raw data. In particular, the sensors 110 may be configured to collect raw data that may be analysed to estimate a motion and mobility of a user, including location, center of mass, body frame, user state, body orientation, skeleton, joints, etc. Accordingly, the sensor(s) 110 may be an infrared depth camera, millimeter wave camera, accelerometer, gyroscope, pedometer, pressure sensor, light sensor, wearable device, etc. In embodiments, the sensors 110 may communicate with the network 108, as illustrated, or with the smart device 120 through means such as WiFi, short-range wireless technology, Near Field communicating (NFC), etc. In general, the sensors 110 may be any device capable of collecting data relating to mobility and movement of a user. The sensors 110 are described in greater detail with respect to FIG. 2-5.

In exemplary embodiments, the smart device 120 includes a mobility assessment client 122 and mobility assessment client data 124, and may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an IoT device, or any other electronic device or computing system capable of sending and receiving data to and from other computing devices. While the smart device 120 is shown as a single device, in other embodiments, the smart device 120 may be comprised of a cluster or plurality of computing devices, in a modular manner, etc., working together or working independently. The smart device 120 is described in greater detail as a hardware implementation with reference to FIG. 3, as part of a cloud implementation with reference to FIG. 4, and/or as utilizing functional abstraction layers for processing with reference to FIG. 5.

The mobility assessment client 122 may act as a client in a client-server relationship, and may be a software and/or hardware application capable of analyzing raw data collected by the sensors 110 as well as computations such as synchronizing data streams and extracting low level features from the raw data. In addition, the mobility assessment client 122 may be further capable of communicating with and providing a user interface for a user to interact with a server and other computing devices via the network 108. Moreover, the mobility assessment client 122 may be further capable of transferring data from the smart device 120 to and from other devices via the network 108. In embodiments, the mobility assessment client 122 may utilize various wired and wireless connection protocols for data transmission and exchange, including short-range wireless technology, 2.4 gHz and 5 gHz internet, near-field communication, Z-Wave, Zigbee, etc. The mobility assessment client 122 is described in greater detail with respect to FIG. 2-5.

The mobility assessment client data 124 may be one or more databases detailing mobility assessment data of one or more users. In particular, the mobility assessment client data 124 may include raw data collected by the sensors 110, and may further include low level user features such as user location, center of mass, body frame, user state, body orientation, etc. The mobility assessment client data 124 is described in greater detail with respect to FIG. 2-5.

In exemplary embodiments, the mobility assessment server 130 includes mobility assessment server data 132 and a mobility assessor 134, and may act as a server in a client-server relationship with the mobility assessment client 122. The mobility assessment server 130 may be an enterprise server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, an IoT device, or any other electronic device or computing system capable of sending and receiving data to and from other computing devices. While the mobility assessment server 130 is shown as a single device, in other embodiments, the mobility assessment server 130 may be comprised of a cluster or plurality of computing devices, in a modular manner, etc., working together or working independently. The mobility assessment server 130 is described in greater detail as a hardware implementation with reference to FIG. 3, as part of a cloud implementation with reference to FIG. 4, and/or as utilizing functional abstraction layers for processing with reference to FIG. 5.

The mobility assessment server data 132 may be one or more databases detailing mobility assessment data of one or more users. In embodiments, the mobility assessment server data 132 may include data relating to trajectory analysis, gait analysis, posture analysis, behaviour analysis, skeleton and joint analysis, etc. Moreover, the mobility assessment server data 132 may further include data relating to mobility parameters and analysis such as location, cadence, path, step interval, step length, walking speed, turning angle, turning speed, leg swing, arm swing, joint load, balance, stability, symmetry, activities, gait stability, slowness, rigidity, tremor, etc. The mobility assessment server data 132 may further include results of analysing the above mobility metrics, e.g., trend and risk prediction relating to health applications such as progression of neuro-degenerative diseases, fall risk assessment, quality of life assessment, frailty of pre- and post-surgery patients, etc.

The mobility assessor 134 may be a software and/or hardware program that may be capable of receiving a configuration, as well as collecting millimeter wave data and depth sensor data. The mobility assessor 134 may be further capable of synchronizing the collected data and extracting low level features therefrom. Moreover, the mobility assessor 134 may be capable of extracting clinical level features from the low level features, as well as generating one or more predictive models based on the extracted clinical level features. The mobility assessor 134 is described in greater detail with reference to FIG. 2-5.

Figure 2:
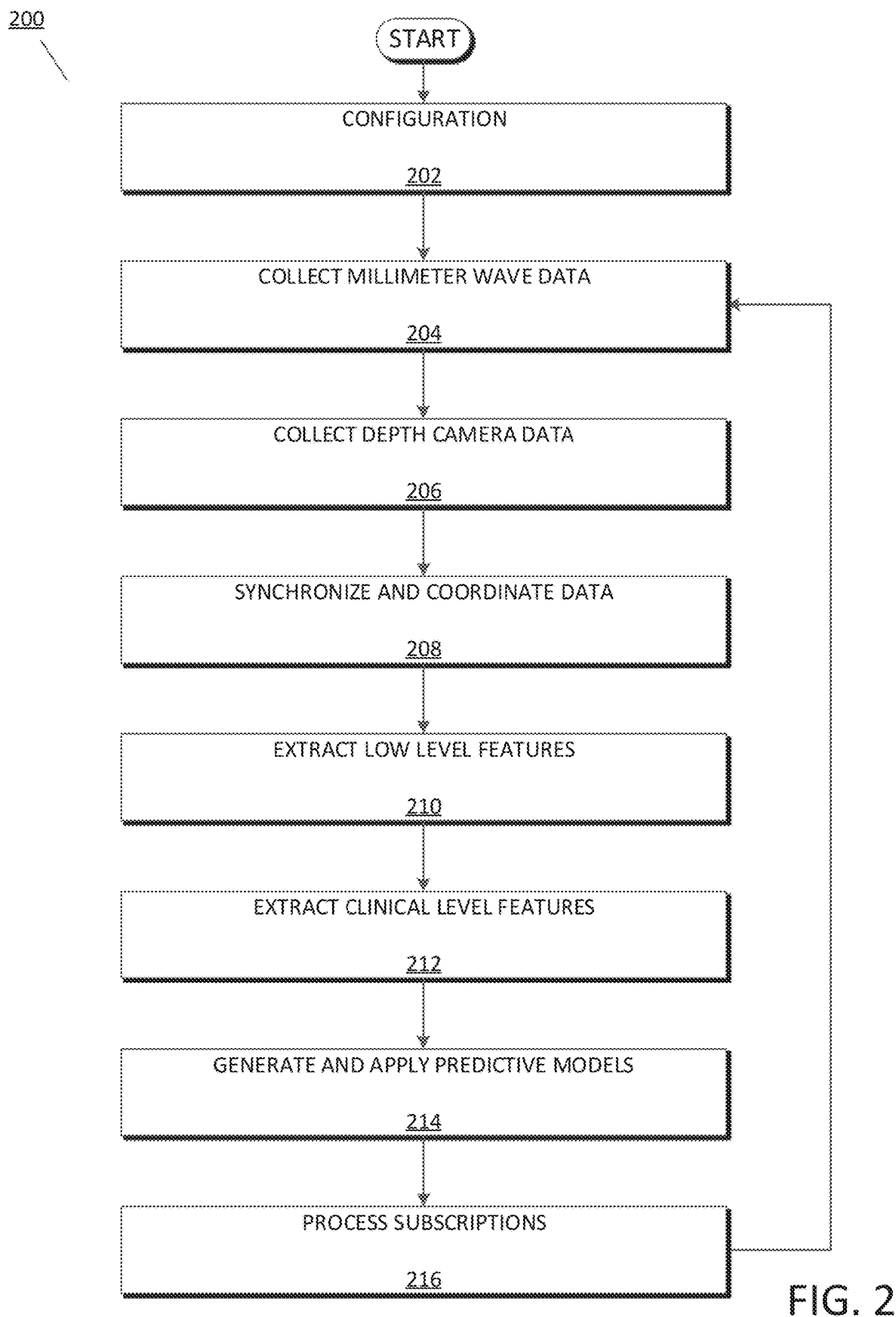
FIG. 2 depicts an exemplary flowchart 200 illustrating the operations of a mobility assessor 134 of the mobility assessment system 100, in accordance with the exemplary embodiments.

FIG. 2 depicts an exemplary flowchart 200 illustrating the operations of the mobility assessor 134 of the mobility assessment system 100, in accordance with the exemplary embodiments.

The mobility assessor 134 may receive a configuration (step 202). In exemplary embodiments, the mobility assessor 134 may be configured by first receiving user registration information based on, for example, log in credentials, internet protocol (IP) address, media access control (MAC) address, etc., via the mobility assessment client 122 and the network 108. The user registration information may include demographic information, such as user name, gender, date of birth, location, etc., as well as health and mobility related data. The health and mobility related data may be received via user/physician input, reference to an electronic health/medical record, etc., and may include one or more user health conditions, baseline user metrics, etc. In addition, receiving the configuration may further include configuring an environment in which the mobility assessment system 100 is implemented, such as mapping and pairing the sensors 110, positioning and calibrating the sensors 110, etc.

In order to better illustrate the operations of the mobility assessor 134, reference is now made to an illustrative example wherein a user utilizes their smart phone to create an account detailing their demographic information and uploads a corresponding electronic health record. In addition, the user configures and pairs an infrared depth camera and millimeter wave sensor within a living room of their home.

The mobility assessor 134 may collect millimeter wave data (step 204). In exemplary embodiments, the millimeter wave data may be collected via the sensor 110 acting as an antenna-based millimeter wave sensor that is capable of detecting objects within an environment and providing range, velocity, and angle thereof. In embodiments, the millimeter wave sensor operates in the small wavelength spectrum, e.g., wavelengths in the 1-10 millimeter range and a frequency range of 30 GHz to 300 GHz, and is therefore capable of penetrating materials such as plastic, drywall, clothing, etc. Moreover, the short wavelengths provide high resolution, resolving distances in the mm range at 60-64 GHz and 76-81 GHz, and such wavelengths are not effected by environmental conditions such as lighting, rain, fog, dust, snow, etc. Using the millimeter wave sensor, the mobility sensor 134 is capable of tracking user and object movement throughout an environment as a user transitions between rooms, behind walls/objects, etc. and recording corresponding data. The data may contain three-dimensional point clouds from which objects, a range/depth of the objects, velocity/acceleration of the objects, angle/orientation of the objects, relative positions of the objects, and the like may be extracted (details forthcoming). In exemplary embodiments, the mobility assessor 134 stores the millimeter wave sensor data locally in the mobility assessment client data 124 such that the mobility assessor 134 may continuously collect large amounts of raw data without the need to transmit the data to the mobility assessment server 130 via the network 108, as well as preserve additional privacy and user control over the data.

Furthering the illustrative example introduced above, the mobility assessor 134 utilizes a millimeter wave sensor to continuously generate and store three-dimensional data points representative of objects within the entire home of the user.

The mobility assessor 134 may collect depth camera data (step 206). In exemplary embodiments, the depth camera data may be collected via the sensor 110 acting as a projector-based depth camera sensor that is capable of detecting objects within a view of the depth camera as well as providing details about the detected objects and the environment, such as a mapping of the objects within the environment. In embodiments, the depth camera sensor operates in the infrared wavelength spectrum, e.g., roughly 700 nm to 1 mm and a frequency range of 430 THz to 300 GHz, and determines a depth of the objects relative to the infrared camera based on calculating time of flight (ToF) to and from the objects using an infrared laser and infrared sensor. Using the depth camera, the mobility assessor 134 is capable of tracking user and object movement within a view of the depth camera and recording such data. The data may include raw RGB and depth streams from which objects, a range/depth of the objects, a mapping of the objects within the viewable environment, and details about the objects (e.g., size, shape, body frame, limbs, joints, etc.) may be extracted (details forthcoming). In exemplary embodiments, the mobility assessor 134 stores the depth camera data locally in the mobility assessment client data 124 such that the mobility assessor 134 may continuously collect large amounts of raw data without the need to transmit the data to the mobility assessment server 130 via the network 108, as well as preserve additional privacy and user control over the data.

Returning to the earlier-introduced example, the mobility assessor 134 utilizes a depth camera to continuously collect an RGB and depth stream of objects within a view of the infrared camera within the living room of the user.

The mobility assessor 134 may synchronize and coordinate the millimeter wave and depth camera data (step 208). In embodiments, the mobility assessor 134 may synchronize the millimeter wave and depth camera data by matching the objects and environment data. The matching may include that of timestamps, depths, sizes/shapes, velocities, angles/orientations, and other data gather by the millimeter wave sensor and depth camera in order to form a seamless and detailed mapping of objects within an environment that takes advantage of the relative strengths of each of the sensors 110. For example, the mobility assessor 134 may reference the depth camera to identify and detail objects such as a user (and components thereof, such as joints, limbs, etc.), chairs, couches, tables, etc, as well as a mapping of the environment, such as floors/walls/rooms, etc. When the user leaves the view of the depth camera, the mobility assessor 134 may then reference the millimeter wave sensor to capture user movement data, for example center of mass, velocity, etc., even through walls and objects. Based on both sets of data, the mobility assessor 134 is capable of tracking and recording object movement seamlessly throughout an environment. Moreover, using the mapping and recorded movements, the mobility assessor 134 may identify and confirm a target within the environment, for example a user, and further deduce user features such as user state (e.g., laying, sitting, standing, walking, etc.), user body orientation, and user location. In the coordination above, the mobility assessor 134 may implement scheduling and dispatching operations that share data gathered by each of the sensors 110 in order to verify and improve upon the data analyses.

With reference again to the formerly introduced example, the mobility assessor 134 coordinates the millimeter wave data and depth camera data to generate a mapping and track movement of objects within the home of the user. Moreover, the mobility assessor 134 identifies the user within the mapping and determines user state, body orientation, and location over time.

The mobility assessor 134 may extract low level features from the coordinated millimeter wave data and the depth camera data (step 210). In exemplary embodiments, the mobility assessor 134 performs all computations to extract low level features locally on the smart device 120, a concept known as edge computing, via the mobility assessment client 122. By edge computing the low level features remotely, the mobility assessor 134 no longer need transmit large amounts of raw millimeter wave and depth camera data to the mobility assessment server 130, saving on data transmission bandwidth. Moreover, by transmitting only low level feature data of the user, rather than the raw data, the mobility assessor 134 preserves additional user privacy by storing user raw data on the premise of the environment in which the mobility assessment system 100 is implemented, for example a home or office, remote from the mobility assessment server 130. In particular, the mobility assessor 134 may extract low level features such as center of mass estimation and user location using the millimeter wave sensor, and target area location and guided body frame, for example user skeleton and joints, from the depth camera data. The mobility assessor 134 may extract the low level features using techniques such as pattern recognition, temporal and spatial analysis, etc.

Continuing the earlier introduced example, the mobility assessor 134 extracts low level features locally that include user center of mass estimation, location, skeleton, and joints.

The mobility assessor 134 may extract clinical level features (step 212). In exemplary embodiments, the mobility assessor 134 may extract clinical features by performing analyses on the extracted low level features. Such analyses may include user trajectories, gait, posture, behaviour, skeletal, joint, etc. data, and the clinical level features may include location, cadence, path, step interval, step length, walking speed, turning angle, turning speed, leg swing, arm swing, joint load, balance, stability, symmetry, activities, etc. The user trajectory analysis may involve the mobility assessor 134 determining a vector path of the user, and include center of mass, velocity, momentum, angular velocity, etc. The mobility assessor 134 may conduct the gait analysis to study and measure user locomotion, such as body mechanics and muscle activity, and utilize techniques such as temporal/spatial, kinematics, markerless gait capture, pressure measurement, kinetics, dynamic electromyography, etc. In addition, the mobility assessor 134 may implement the posture analysis by measuring head, shoulder, and hip position to determine a posture of the user. The mobility assessor 134 may further perform skeletal and joint analysis to identify bones and joints of the user, as well as joint loads, degrees of motion, etc. thereof. In exemplary embodiments, the mobility assessor 134 may analyse the low level features on the mobility assessment server 130 such that the mobility assessment client 122 need only transmit low level feature data to the mobility assessment server 140.

With reference to the previously introduced example, the mobility assessor 134 analyses the low level features to extract clinical level features that include location, cadence, path, step interval, step length, walking speed, turning angle, turning speed, leg swing, arm swing, joint load, balance, stability, and symmetry.

The mobility assessor 134 may generate and apply predictive models (step 214). In exemplary embodiments, the mobility assessor 134 may generate one or more predictive models that correlate the clinical level features with one or more health conditions, such as progression of neuro-degenerative diseases, fall risk assessment, quality of life assessment, frailty of pre- and post-surgery patients, etc. The mobility assessor 134 may train the predictive models through techniques such as machine learning, including regression methods, Random Forest, Markov Chain Monte Carlo, neural networks, etc. In such embodiments, the mobility assessor 134 may weight the clinical level features based on training data in a model that identifies and computes the clinical level features into a score representative of a health condition mentioned above. Moreover, the mobility assessor 134 may modify the predictive models, for example modifying a weight associated with a particular feature, based on received feedback, for example subsequent data collection affirming or refuting a score.

In furthering the example introduced above, the mobility assessor 134 applies a model to the clinical level features to determine how the user responded to new Parkinson's disease medication.

The mobility assessor 134 may process subscriptions (step 216). In embodiments, the mobility assessor 134 may publish clinical level features for subscribed and approved healthcare applications.

Concluding the aforementioned example, the mobility assessor 134 publishes the clinical level features balance and stability subscribed to by a healthcare application that monitors risk of fall.

Figure 3:
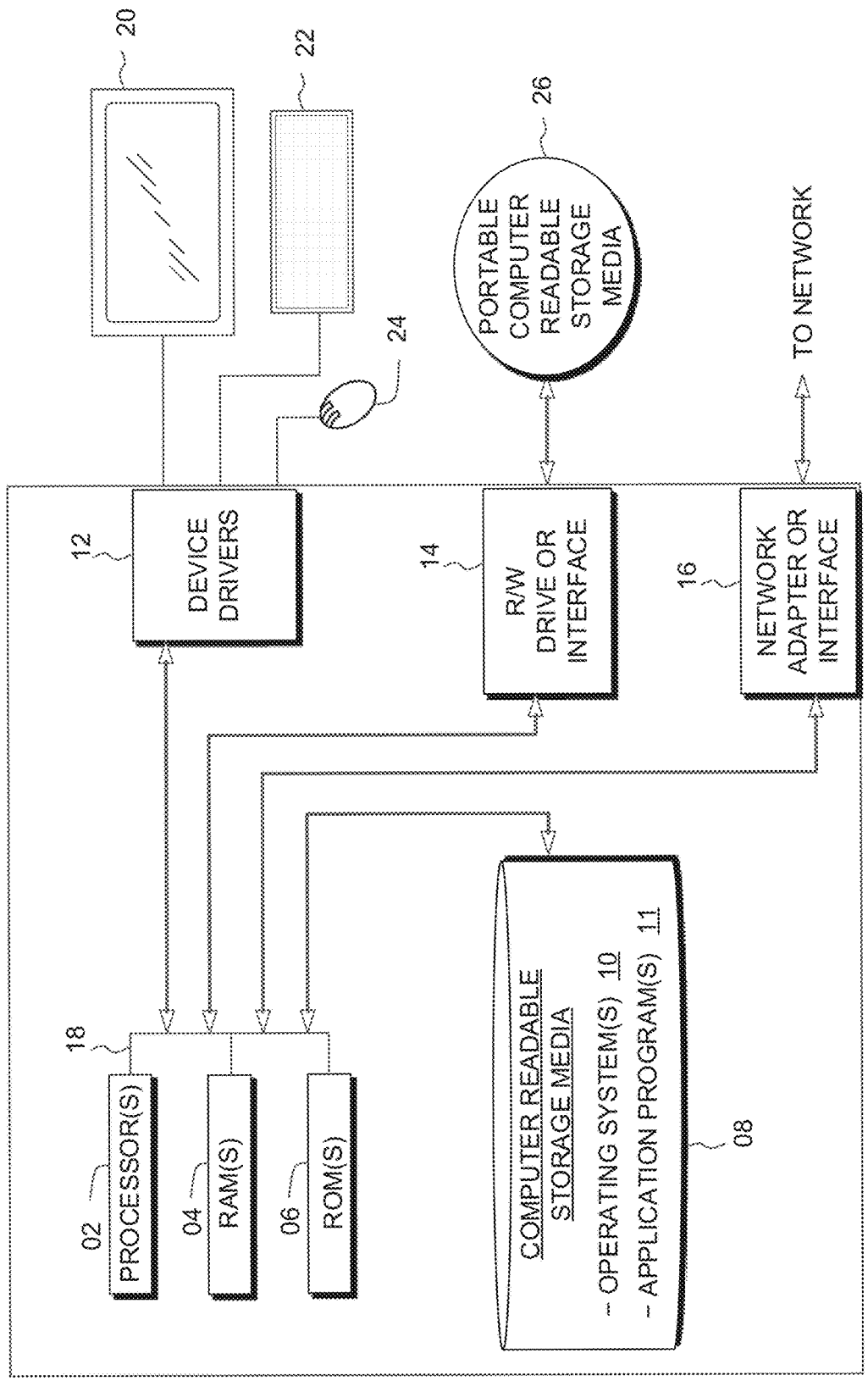
FIG. 3 depicts an exemplary block diagram depicting the hardware components of the mobility assessment system 100 of FIG. 1, in accordance with the exemplary embodiments.
Figure 5:
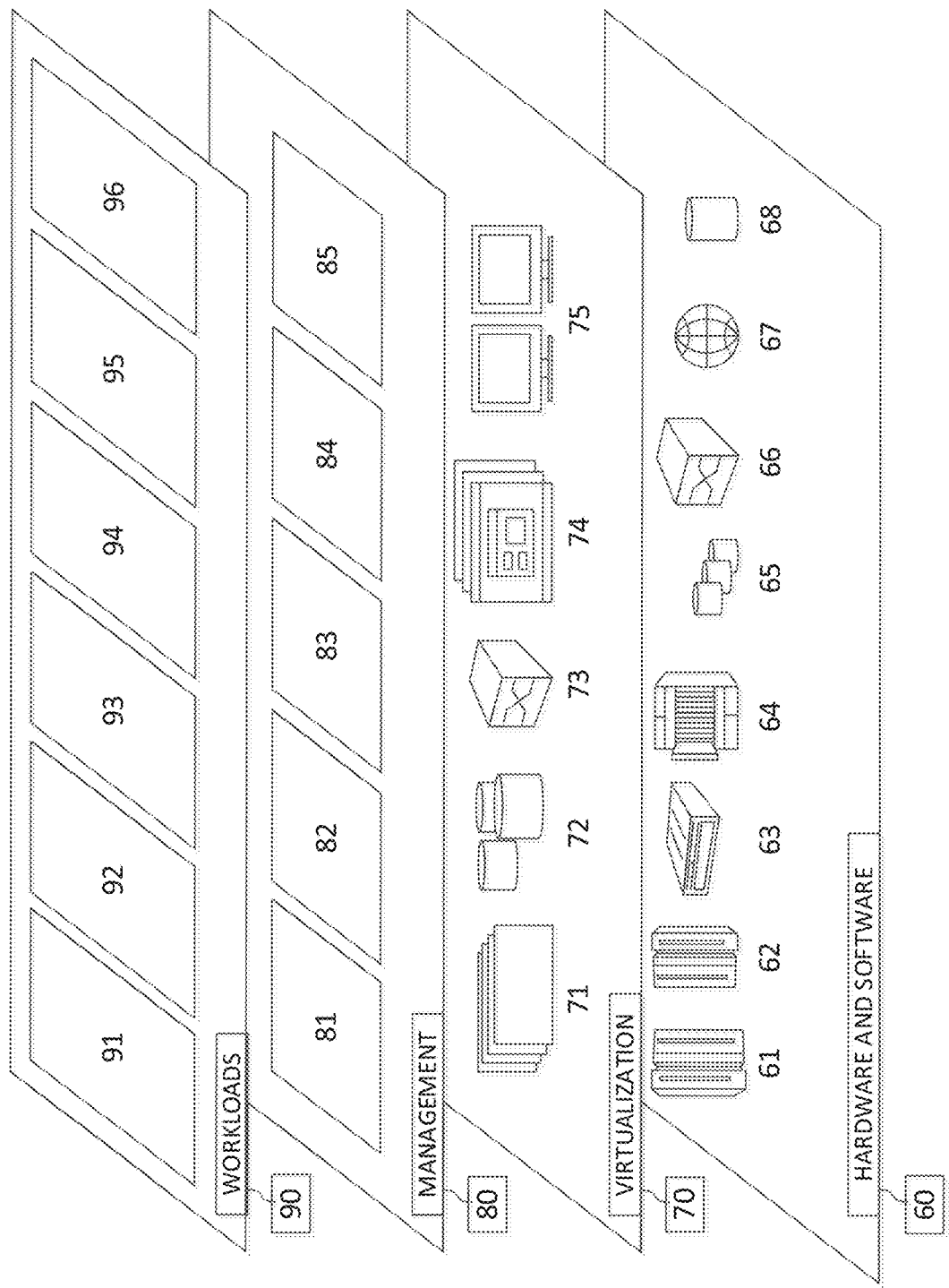
FIG. 5 depicts abstraction model layers, in accordance with the exemplary embodiments.

FIG. 3 depicts a block diagram of devices used within mobility assessment system 100 of FIG. 1, in accordance with the exemplary embodiments. It should be appreciated that FIG. 5 provides only an illustration of one implementation and does not imply any limitations with regard to the environments in which different embodiments may be implemented. Many modifications to the depicted environment may be made.

Devices used herein may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11 are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Devices used herein may also include a R/W drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Devices used herein may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Devices used herein may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific one of the exemplary embodiments. However, it should be appreciated that any particular program nomenclature herein is used merely for convenience, and thus the exemplary embodiments should not be limited to use solely in any specific application identified and/or implied by such nomenclature.

Based on the foregoing, a computer system, method, and computer program product have been disclosed. However, numerous modifications and substitutions can be made without deviating from the scope of the exemplary embodiments. Therefore, the exemplary embodiments have been disclosed by way of example and not limitation.

It is to be understood that although this disclosure includes a detailed description on cloud computing, implementation of the teachings recited herein are not limited to a cloud computing environment. Rather, the exemplary embodiments are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or data center).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 4:
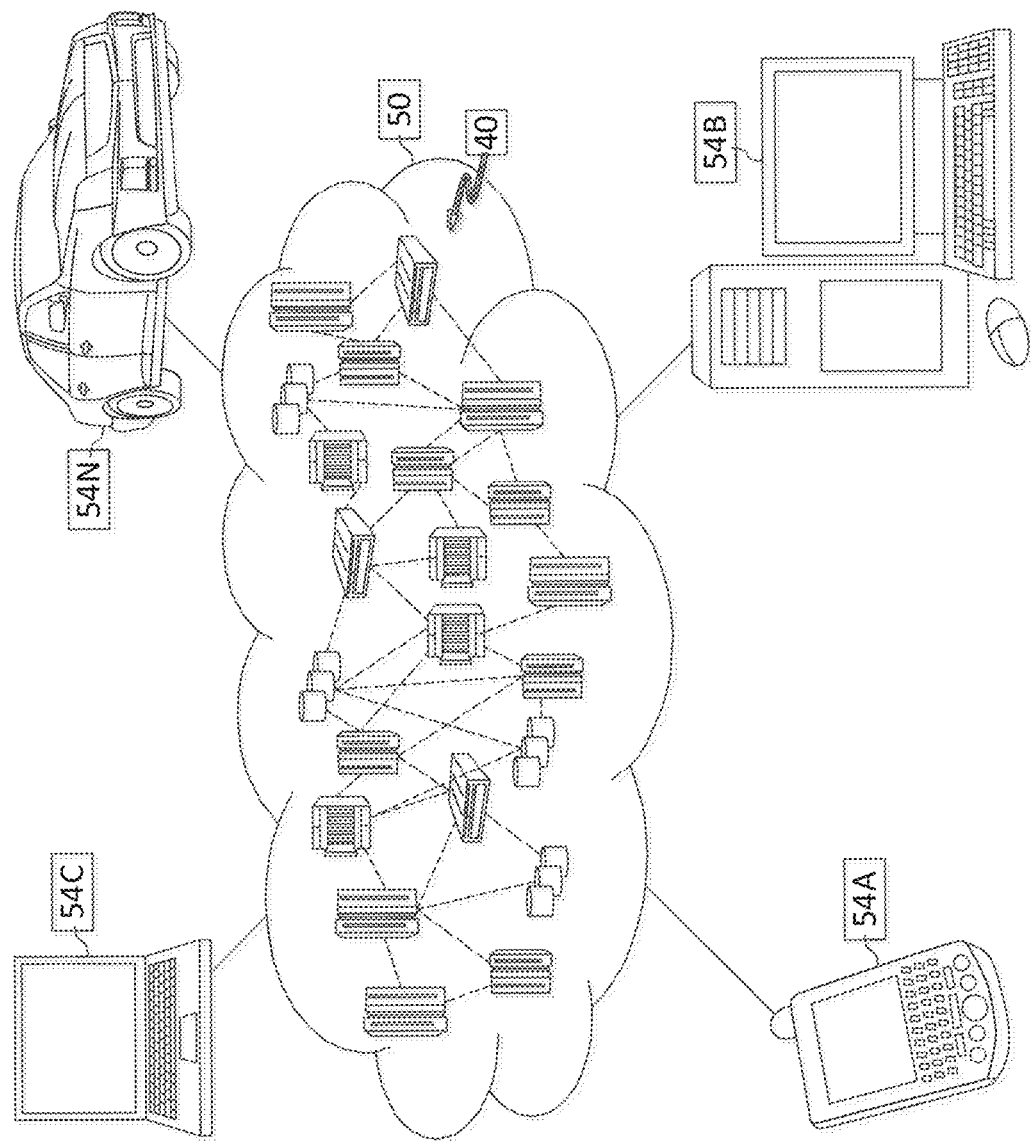
FIG. 4 depicts a cloud computing environment, in accordance with the exemplary embodiments.

Referring now to FIG. 4, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 40 and cloud computing environment 50 can communicate with any type of computerized device over any type of network and/or network addressable connection (e.g., using a web browser).

Referring now to FIG. 5, a set of functional abstraction layers provided by cloud computing environment 50 (FIG. 4) is shown. It should be understood in advance that the components, layers, and functions shown in FIG. 5 are intended to be illustrative only and the exemplary embodiments are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and mobility processing 96.

The exemplary embodiments may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A computer-implemented method for assessing user mobility, the method comprising:
    collecting mobility data corresponding to a user that includes joint, limb, and movement data via a millimeter wave sensor and a depth camera positioned within an environment of the user, wherein the movement data is collected via the millimeter wave sensor while the joint and limb data is collected via the depth camera;
    extracting one or more low level features from the mobility data;
    extracting one or more clinical level features from the low level features; and
    assessing one or more health conditions of the user based on applying one or more models to the one or more clinical level features.

2. The method of claim 1, wherein extracting the one or more low level features is performed on a local computing device, and wherein extracting the one or more clinical level features from the one or more low level features is performed on a remote computing device, and further comprises:
    transmitting the one or more low level features from the local computing device to the remote computing device.

3. The method of claim 1, further comprising:
synchronizing the mobility data collected by the millimeter wave sensor and the depth camera.

4. The method of claim 1, wherein the one or more low level features are selected from a group consisting of center of mass estimation, location, skeleton, and joints.

5. The method of claim 1, wherein the one or more clinical level features are selected from a group consisting of cadence, path, step interval, step length, walking speed, turning angle, turning speed, leg swing, arm swing, joint load, balance, stability, and symmetry.

6. The method of claim 1, wherein the one or more health conditions are selected from a group consisting of progression of neuro-degenerative diseases, fall risk assessment, quality of life assessment, and frailty of pre- and post-surgery patients.

7. A computer program product for assessing user mobility, the computer program product comprising:
one or more non-transitory computer-readable storage media and program instructions stored on the one or more non-transitory computer-readable storage media capable of performing a method, the method comprising:
collecting mobility data corresponding to a user that includes joint, limb, and movement data via a millimeter wave sensor and a depth camera positioned within an environment of the user, wherein the movement data is collected via the millimeter wave sensor while the joint and limb data is collected via the depth camera;
extracting one or more low level features from the mobility data;
extracting one or more clinical level features from the low level features; and
assessing one or more health conditions of the user based on applying one or more models to the one or more clinical level features.

8. The computer program product of claim 7, wherein extracting the one or more low level features is performed on a local computing device, and wherein extracting the one or more clinical level features from the one or more low level features is performed on a remote computing device, and further comprises:
transmitting the one or more low level features from the local computing device to the remote computing device.

9. The computer program product of claim 7, further comprising:
synchronizing the mobility data collected by the millimeter wave sensor and the depth camera.

10. The computer program product of claim 7, wherein the one or more low level features are selected from a group consisting of center of mass estimation, location, skeleton, and joints.

11. The computer program product of claim 7, wherein the one or more clinical level features are selected from a group consisting of cadence, path, step interval, step length, walking speed, turning angle, turning speed, leg swing, arm swing, joint load, balance, stability, and symmetry.

12. The computer program product of claim 7, wherein the one or more health conditions are selected from a group consisting of progression of neuro-degenerative diseases, fall risk assessment, quality of life assessment, and frailty of pre- and post-surgery patients.

13. A computer system for assessing user mobility, the system comprising:
one or more computer processors, one or more computer-readable non-transitory storage media, and program instructions stored on the one or more of the computer-readable storage media for execution by at least one of the one or more processors capable of performing a method, the method comprising:
collecting mobility data corresponding to a user that includes joint, limb, and movement data via a millimeter wave sensor and a depth camera positioned within an environment of the user, wherein the movement data is collected via the millimeter wave sensor while the joint and limb data is collected via the depth camera;
extracting one or more low level features from the mobility data;
extracting one or more clinical level features from the low level features; and
assessing one or more health conditions of the user based on applying one or more models to the one or more clinical level features.

14. The computer system of claim 13, wherein extracting the one or more low level features is performed on a local computing device, and wherein extracting the one or more clinical level features from the one or more low level features is performed on a remote computing device, and further comprises:
transmitting the one or more low level features from the local computing device to the remote computing device.

15. The computer system of claim 13, further comprising:
synchronizing the mobility data collected by the millimeter wave sensor and the depth camera.

16. The computer system of claim 13, wherein the one or more low level features are selected from a group consisting of center of mass estimation, location, skeleton, and joints.

17. The computer system of claim 13, wherein the one or more clinical level features are selected from a group consisting of cadence, path, step interval, step length, walking speed, turning angle, turning speed, leg swing, arm swing, joint load, balance, stability, and symmetry.

* * * * *